(12) United States Patent
Demierre et al.

(10) Patent No.: US 9,333,501 B2
(45) Date of Patent: *May 10, 2016

(54) METHOD FOR PRODUCING STRUCTURED MICROCARRIERS

(71) Applicant: MYCARTIS NV, Zwijnaarde/Ghent (BE)

(72) Inventors: Nicolas Demierre, Chatel-St-Denis (CH); Stephan Gamper, Lausanne (CH); Raphael Tornay, Illarsaz (CH); Philippe Renaud, Lausanne (CH)

(73) Assignee: MYCARTIS NV, Zwijnaarde/Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,513

(22) PCT Filed: Jul. 22, 2013

(86) PCT No.: PCT/EP2013/065446
§ 371 (c)(1),
(2) Date: Jan. 13, 2015

(87) PCT Pub. No.: WO2014/016263
PCT Pub. Date: Jan. 30, 2014

(65) Prior Publication Data
US 2015/0190803 A1  Jul. 9, 2015

(30) Foreign Application Priority Data

Jul. 24, 2012 (EP) .................................. 12177715

(51) Int. Cl.
*B01L 3/00* (2006.01)
*G01N 15/14* (2006.01)

(52) U.S. Cl.
CPC ..... *B01L 3/502707* (2013.01); *B01L 3/502761* (2013.01); *B01L 3/545* (2013.01);

(Continued)

(58) Field of Classification Search
None
See application file for complete search history.

(56) References Cited

U.S. PATENT DOCUMENTS 6,963,530 B1 * 11/2005 Thornton ............... G11B 7/127
   369/121
8,097,926 B2 * 1/2012 De Graff ........... H01L 27/14618
   257/419

(Continued)

FOREIGN PATENT DOCUMENTS

| GB | 2 427 022 | 12/2006 | ............... G02B 5/18 |
| WO | WO 00/63695 | 10/2000 | ........... G01N 33/532 |
| WO | WO 2010/072011 | 7/2010 | ................ B01L 3/00 |
| WO | WO 2012/106827 | 8/2012 | ................ B01L 3/00 |

OTHER PUBLICATIONS

International Search Report for International Application No. PCT/EP2013/065446, Oct. 17, 2013.

(Continued)

*Primary Examiner* — Allan Olsen
(74) *Attorney, Agent, or Firm* — Kusner & Jaffe (57) ABSTRACT

The present invention relates to a method for producing microcarriers, the method comprising the steps of providing a wafer having a bottom layer, a top layer and an insulating layer, structuring the top layer to define at least one three-dimensional structure on the top surface of the top layer, etching away the top layer to delineate lateral walls of bodies of the microcarriers, applying a continuous polymer layer over the top surface of the bodies of the microcarriers, removing the bottom layer and the insulating layer, structuring the bottom surfaces of the bodies of the microcarriers to define at least one three-dimensional structure on the bottom surface of each body, and removing the polymer layer to release the microcarriers.

18 Claims, 6 Drawing Sheets

(52) U.S. Cl.
CPC ..... *G01N15/1456* (2013.01); *B01L 2200/0647* (2013.01); *B01L 2200/10* (2013.01); *B01L 2200/12* (2013.01); *B01L 2300/0803* (2013.01); *B01L 2300/0819* (2013.01); *B01L 2300/0893* (2013.01); *B01L 2300/16* (2013.01)

(56) References Cited

U.S. PATENT DOCUMENTS

| | | | |
|---|---|---|---|
| 8,953,314 B1* | 2/2015 | Fedorov | H01L 23/44 257/707 |
| 2001/0041369 A1 | 11/2001 | Chang et al. | 436/518 |
| 2003/0140713 A1* | 7/2003 | Ohsato | G01L 5/162 73/862.041 |
| 2005/0244955 A1 | 11/2005 | Li et al. | 435/287.2 |
| 2010/0246005 A1 | 9/2010 | Moon et al. | 359/569 |
| 2012/0152322 A1* | 6/2012 | Kribus | H01L 31/0687 136/249 |

OTHER PUBLICATIONS

Bhardwaj et al., "Advanced silicon etching using high density plasmas," SPIE vol. 2639, 224 (1995).

Schilp et al., "Advanced Etch Tool for High Etch Rate Deep Reactive Ion Etching in Silicon Micromachining Production Environment," Proceeding MST 2001.

Madou, 2002, "Deep Reactive Ion Etching (DRIE)," Fundamentals of Microfabrication, CRC Press, pp. 105-106.

* cited by examiner

METHOD FOR PRODUCING STRUCTURED MICROCARRIERS

FIELD OF THE INVENTION

The invention relates to a microcarrier and to a method for producing microcarriers. The invention concerns in particular microcarriers suitable for performing a biological and/or a chemical assay for research and clinical laboratories.

BACKGROUND OF THE INVENTION

Within the scope of the present invention, a microcarrier or a microparticle refers to any type of particles, respectively to any type of carriers, microscopic in size, typically with the largest dimension being from 100 nm to 300 µm, preferably from 1 µm to 200 µm.

According to the present invention, the term microcarrier refers to a microparticle functionalized, or adapted to be functionalized, that is containing, or adapted to contain, one or more ligands or functional units bound to the surface of the microcarrier or impregnated in its bulk. A large spectrum of chemical and biological molecules may be attached as ligands to a microcarrier. A microcarrier can have multiple functions and/or ligands. As used herein, the term functional unit is meant to define any species that modifies, attaches to, appends from, coats or is covalently or non-covalently bound to the surface of said microcarrier or impregnated in its bulk. These functions include all functions that are routinely used in high-throughput screening technology and diagnostics.

Drug discovery or screening and DNA sequencing commonly involve performing assays on very large numbers of compounds or molecules. These assays typically include, for instance, screening chemical libraries for compounds of interest or particular target molecules, or testing for chemical and biological interactions of interest between molecules. Those assays often require carrying out thousands of individual chemical and/or biological reactions.

Numerous practical problems arise from the handling of such a large number of individual reactions. The most significant problem is probably the necessity to label and track each individual reaction.

One conventional method of tracking the identity of the reactions is achieved by physically separating each reaction in a microtiter plate (microarray). The use of microtiter plates, however, carries several disadvantages like, in particular, a physical limitation to the size of microtiter plates used, and thus to the number of different reactions that may be carried out on the plates.

In light of the limitations in the use of microarrays, they are nowadays advantageously replaced by functionalized encoded microparticles to perform chemical and/or biological assays. Each functionalized encoded microparticle is provided with a code that uniquely identifies the particular ligand(s) bound to its surface. The use of such functionalized encoded microparticles allows for random processing, which means that thousands of uniquely functionalized encoded microparticles may all be mixed and subjected to an assay simultaneously. Examples of functionalized encoded microparticles are described in the international patent application WO 00/63695 and are illustrated in FIG. 1.

The international patent application WO 2010/072011 describes an assay device having at least a microfluidic channel which serves as a reaction chamber in which a plurality of functionalized encoded microparticles or microcarriers 1 (FIG. 1) can be packed. The microfluidic channel is provided with stopping means acting as filters that allow a liquid solution containing chemical and/or biological reagents to flow through while blocking the microcarriers 1 inside. The geometrical height of said microfluidic channels and the dimensions of said microcarriers 1 are chosen so that said microcarriers 1 are typically arranged in a monolayer arrangement inside each microfluidic channel preventing said microcarriers 1 to overlap each other.

Those functionalized encoded microcarriers 1 that show a favorable reaction of interest between their attached ligand(s) and the chemical and/or biological reagents flowing through may then have their code read, thereby leading to the identity of the ligand that produced the favorable reaction.

Figure 1:
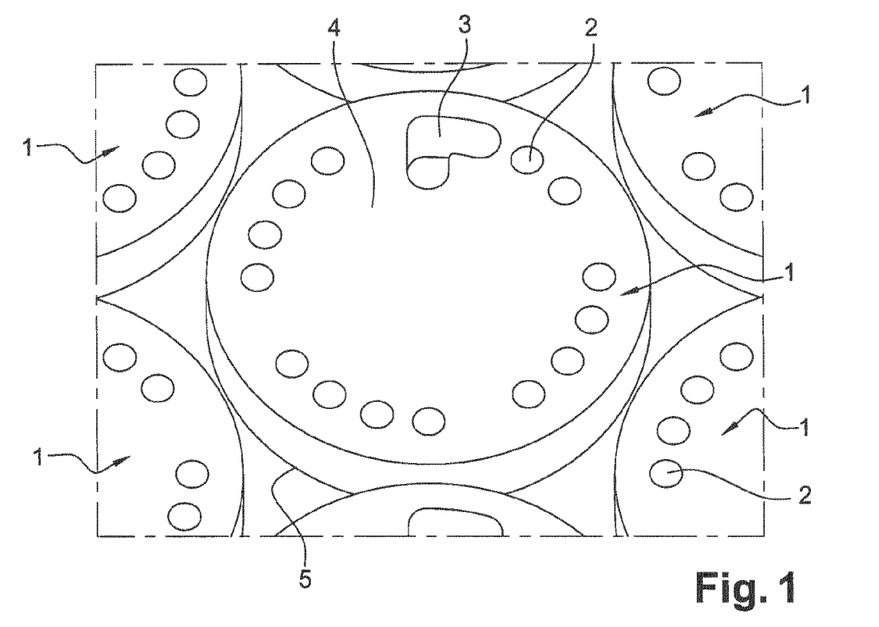
FIG. 1 illustrates a top perspective view of microcarriers according to the prior art.

The code may comprise a distinctive pattern including a plurality of traversing holes 2 and an asymmetric orientation mark such as, for example, a L-shaped sign 3 (as shown in FIG. 1) or a triangle. This asymmetric orientation mark allows the distinction between the top surface 4 and the bottom surface 5 of the microcarrier 1.

The term microfluidic channel refers to a closed channel, i.e. an elongated passage for fluids, with a cross-section microscopic in size, i.e. with the smallest dimension of the cross-section being typically from about 1 to about 500 micrometers, preferably about 10 to about 200 micrometers. A microfluidic channel has a longitudinal direction, that is not necessarily a straight line, and that corresponds to the direction in which fluids are flowing within the microfluidic channel, i.e. preferably essentially to the direction corresponding to the average speed vector of the fluid, assuming a laminar flow regime.

With the assay device described in WO 2010/072011, the detection of a reaction of interest can be based on continuous readout of the fluorescence intensity of each encoded microcarrier 1 present in a microfluidic channel. In other words, the presence of a target molecule in the assay will trigger a predetermined fluorescent signal.

However, the functionalized encoded microparticles 1 and the assay device described in WO 2010/072011 do not allow for rapid quantification of reagent or ligand before an equilibrium state is reached, when the fluorescent signals saturate. Although the assay device of WO 2010/072011 decreases the time needed to reach equilibrium, in typical concentration values of analyte in the nano-molar range, ten to twenty minutes are still required, while lower concentration in the pico-molar range can take up to hours to be reached and serve for quantification. Moreover, the discrepancies in their fluorescent signals, in particular the diffusion pattern even after the equilibrium has been reached do not determine a quantitative information with a lower margin of error than about 15%.

Figure 2:
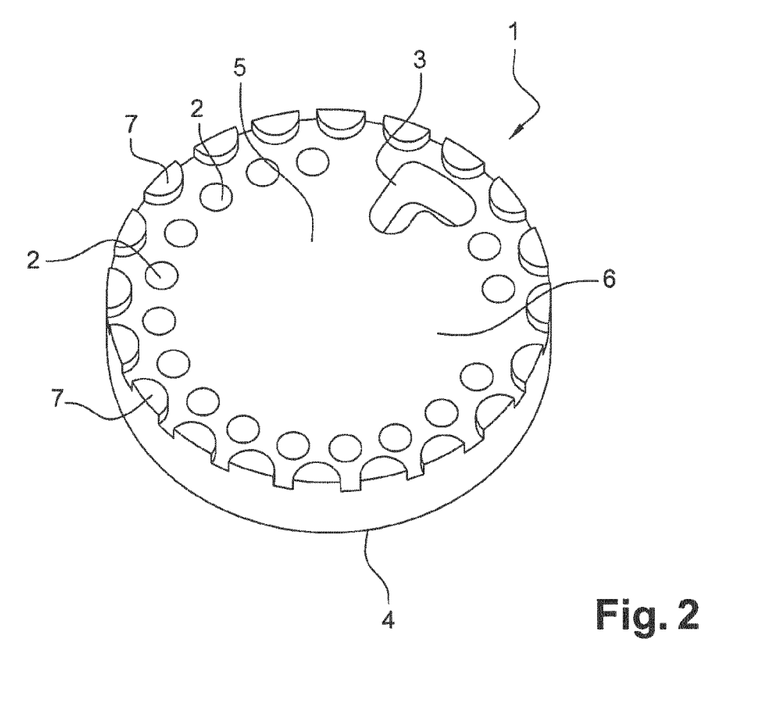
FIG. 2 illustrates a bottom perspective view of a microcarrier according to the prior art, having spacing elements protruding from a bottom surface of the microcarrier.
Figure 3:
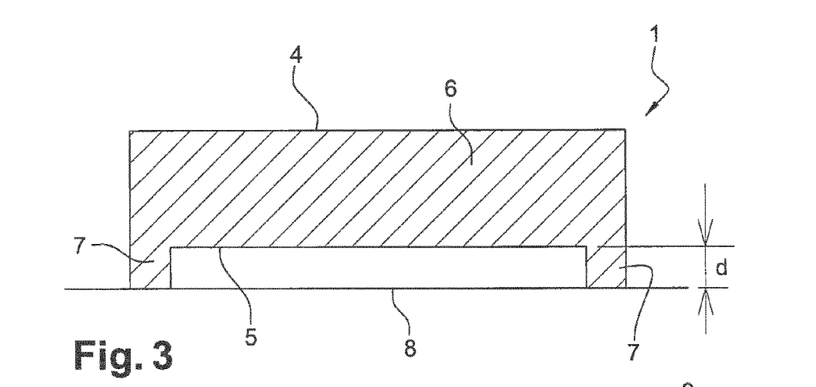
FIG. 3 illustrates a cross-section view of the microcarrier shown in FIG. 2.

To remedy these drawbacks, the patent application PCT/CH2012/000032 proposes an encoded microcarrier, shown in FIGS. 2 and 3, comprising a body 6 having a shape of a right circular cylinder and comprising a top surface 4, a bottom surface 5 and spacing elements 7 protruding from the bottom surface 5.

The microcarrier 1 with its spacing elements 7 is shaped to ensure that, when the encoded microcarrier 1 is laid on a flat plane 8 with the detection surface 5 facing said plane 8, a gap d exists between said flat plane 8 and the detection surface 5, as shown in FIG. 3.

As said above, the encoded microcarrier contains one or more ligands bound to the bottom surface 5 (detection surface). When contacting the ligand-bound encoded microcarrier 1 with a solution that may contain one or more target analytes, a reaction of interest may occur on the detection surface 5, depending on the presence or absence of a proper analyte. As an example, a reaction of interest can emit or inhibit a fluorescent signal, which can be monitored. Detecting a reaction on the detection surface 5 can allow determining the presence or absence of particular analytes of interest.

Figure 4:
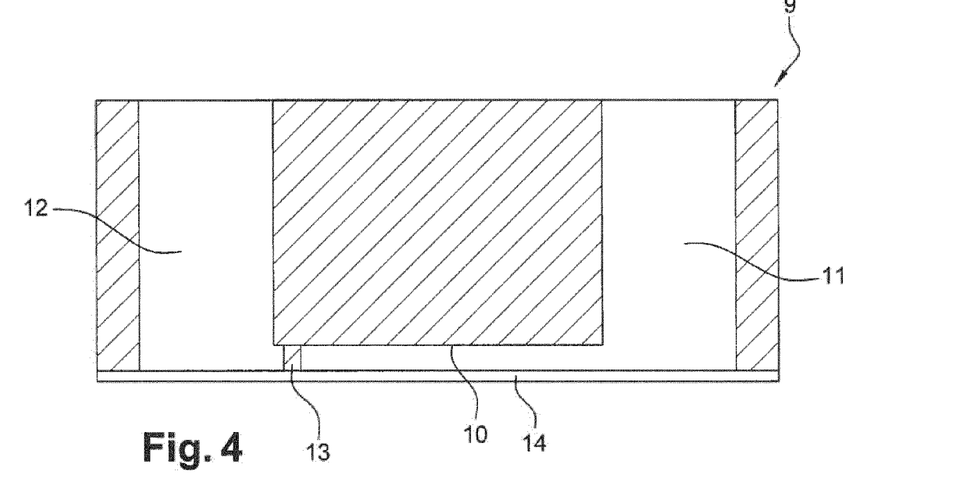
FIG. 4 illustrates a cross-section view of a microfluidic channel of an assay device according to the prior art.
Figure 5:
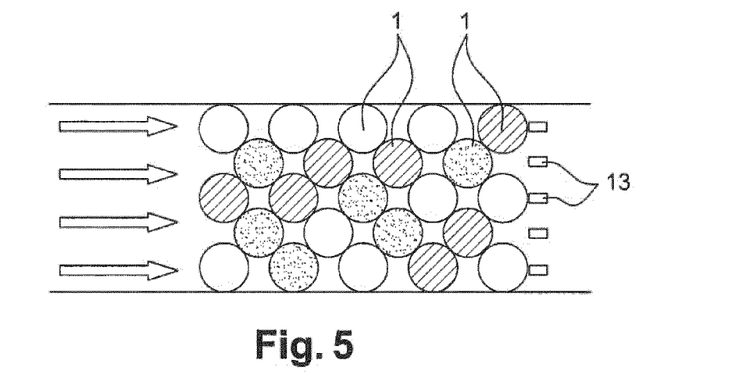
FIG. 5 illustrates a top view of encoded microcarriers loaded in the microfluidic channel of FIG. 4.

The document PCT/CH2012/000032 also discloses an assay system comprising a plurality of encoded microcarriers 1 with spacing elements and an assay device, partially shown in FIGS. 4 and 5. The assay device 9 has at least one microfluidic channel 10 having an inlet connected to an inlet well 11 and an outlet connected to an outlet well 12, said channel 10 being shaped to accommodate a plurality of said encoded microcarriers 1. The microfluidic channel 10 is provided with stopping means 13 arranged in the vicinity of the outlet of the microfluidic channel 10 and acting as a filter that allow a liquid solution to flow through while blocking said encoded microcarriers 1 inside. The microfluidic channel 10 has a cross-section that allows at least two encoded microcarriers 1 to be arranged side by side over the length of said microfluidic channel 10, in a monolayer arrangement as depicted in FIG. 5. The microfluidic channel 10 comprises at least an observation wall 14 through which an assay is monitorable. Typically, when the assay is monitored by fluorescent signal, the observation wall is transparent.

In such an assay system, when the encoded microcarriers are loaded in the microfluidic channel 10 with said detection surface 5 facing said observation wall 14, the spacing elements 7 generate a gap d between said detection surface 5 and said observation wall 14 to allow a circulation of liquid in said gap d, said liquid containing chemical and/or biological reagent of interest for the assay.

Thus, the spacing elements 7 permit a homogeneous convective flow all over the microfluidic channel 10 resulting in homogeneous fluorescent increase over time and across encoded microcarriers 1. The homogeneous signal increase allows for a rapid quantification of the analyte being flushed, from the first seconds, by monitoring the fluorescence rate.

When microcarriers 1 are introduced into the inlet well 11, said microcarriers 1 may flip over during their sedimentation in the well 11. Thus, some of the microcarriers 1 have their detection surface 5 opposite to the detection wall 14 of the microchannel 10. However, the detection of the presence of molecules bound to the detection surface 5 such as by fluorescence microscopy is possible only when said surface 5 is facing the detection wall 11. Thus, microcarriers 1 having a wrong orientation do not emit any detectable signal.

Moreover, the laminar fluid flow is disturbed by the microcarriers 1 which are not properly oriented. Indeed, in this case, said laminar fluid flow is forced to move around the concerned microcarriers 1, thus creating disturb the homogeneity of the fluid velocity along the microchannel 10, thereby disturbing the homogeneous distribution of the reagents and target molecules intended to interact with the detection surfaces 5 of the microcarriers 1. This affects the reliability of the assay.

More generally, the same orientation problem could arise with other kind of microcarriers having only one of the bottom and top surfaces provided with a three-dimensional structure.

SUMMARY OF THE INVENTION

The present invention aims to remedy all or part of the disadvantages mentioned above.

To this aim, the invention proposes a method for producing microcarriers, the method comprising the following steps:

(a) providing a wafer having a sandwich structure comprising a bottom layer, a top layer and an insulating layer located between said bottom and top layers, (b) structuring the top layer to define at least one three-dimensional structure on the top surface of the top layer, (c) etching away the top layer to delineate lateral walls of bodies of the microcarriers, each body comprising at least one three-dimensional structure on its top surface, (d) applying a continuous polymer layer over the top surface of the bodies of the microcarriers, (e) removing the bottom layer and the insulating layer, (f) structuring the bottom surfaces of the bodies of the microcarriers to define at least one three-dimensional structure on the bottom surface of each body, (g) removing the polymer layer to release the microcarriers.

The microcarriers obtained by the method according to the invention comprise three-dimensional structures on both top and bottom surfaces. Thus, when these microcarriers are used in the above mentioned microchannel, the formation of a turbulent fluid flow during a biological and/or chemical assay is prevented and a laminar fluid flow is maintained throughout the microchannel, whatever the orientation of the microcarriers in the microchannel.

It should be noted that the polymer layer applied in step (d) protects the three-dimensional structures of the top layer while etching the bottom layer and the insulating layer (step (e)) and while structuring the bottom surfaces of the bodies of the microcarriers (step (f)).

The polymer layer also maintains the bodies altogether during step (e) and (f) and prevents their dispersion in sensitive parts of the equipment used for their preparation, like for instance in the turbo-pumps.

The method may comprise a step of depositing a first active layer on the top surfaces of the bodies of the microcarriers before step (d).

The method may also comprise a step of depositing a second active layer on the bottom surfaces of the bodies of the microcarriers before step (g).

For example, the first active layer and/or the second active layer comprise a material having optical or magnetic properties, polycrystalline silicon and/or polytetrafluoroethylene, or a metallic layer having a high reflective index.

Using a material having optical properties will increase substantially the fluorescent signal emitted from the corresponding surface of the microcarrier. A material having magnetic properties can be used to orientate the microcarrier in a desired direction, for example. The use of polycrystalline silicon increases the porosity of the corresponding surface of the body in order to increase the effective area to be coated on said surface. Finally, polytetrafluoroethylene can be used to reduce the friction between the microcarrier and the surface on which it rests during the assay.

The first active layer and/or the second active layer may comprise an oxide or a nitride, for example silicon dioxide, or a metal layer.

Silicon dioxide may be used to smooth the corresponding surface of the body and to increase sliding of non-specific molecules on said surface. The specific signal emitted by the molecules bound to said surface is therefore enhanced while the interfering signal emitted by non-specific molecules is considerably lowered.

According to an embodiment of the invention, the three-dimensional structure of the top surface and/or the three-dimensional structure of the bottom surface comprise at least one spacing element protruding from the corresponding surface.

Said spacing element provides a gap between the corresponding surface of the microcarrier and the surface on which said microcarrier rests, in order to create a laminar fluid flow through said microchannel.

According to another embodiment of the invention, the three-dimensional structure of the top surface and/or the three-dimensional structure of the bottom surface comprise at least one diffraction grating.

The diffraction grating refers to a structure designed to split and diffracts light into several beams travelling in different directions. The diffraction grating generates a surface plasmon resonance (and thus a detectable signal) on the top surface and/or on the bottom surface of the microcarrier when illuminated by light. Moreover, the diffraction grating is intended to interact with target molecules inducing variations of the surface plasmon resonance. These variations can be detected to determine the presence or the absence of said target molecules. The document GB 2 427 022 discloses a microcarrier having only one surface comprising a diffraction grating.

According to still another embodiment, the three-dimensional structure of the top surface and/or the three-dimensional structure of the bottom surface comprise at least one nanostructure having a nanoscale depth.

In an embodiment, the nanostructure having a nanoscale depth comprises nano-pillars dispersed uniformly on the top surface. The nanoscale depth of the nanostructure contributes to increase the efficiency in receiving and radiating light. The nanostructure with nanoscale depth can also concentrate the light to confined regions to create strong local electric field, which enhances fluorescence emitted from the nanostructured surface.

Additionally, the polymer layer may comprise parylen.

The parylen layer is a highly resistant layer capable of maintaining the microcarriers before releasing.

In a variant, the polymer layer is a glue layer which binds a support, for example a wafer made of silicon, quartz or glass, to the wafer.

The use of a support bound to the wafer provides enhanced mechanical properties in order to facilitate the handling of the wafer during the production of the microcarriers.

According to a technical feature of the invention, step (e) is made by a first etching for etching selectively the bottom layer, for example by using an etching bath, and by a second etching for etching selectively the insulating layer, for example by a dry etching.

If the bottom layer comprises monocrystalline silicon, the etching bath may be a potassium hydroxide bath. In addition, if the insulating layer comprises silicon dioxide, the dry etching could be made by plasma etching of $CHF_3$ (fluoroform) or by plasma etching of $CF_4$.

The polymer layer may also be etched by dry etching. For example, if the polymer layer comprises parylen, it may be etched by oxygen plasma.

The invention also relates to a microcarrier obtained by the method according to the invention, the microcarrier comprising a body having a top surface and a bottom surface, each of said surfaces comprising a three-dimensional structure.

BRIEF DESCRIPTION OF THE DRAWINGS

The invention can be better understood and other details, features, and advantages of the invention appear on reading the following description made by way of non-limiting examples with reference to the accompanying drawings, in which:

FIGS. 6 to 17 illustrate the successive steps of the method for producing microcarriers according to an embodiment the invention;

DETAILED DESCRIPTION OF THE INVENTION

A method for producing microcarriers according to the invention will be described with reference to FIGS. 6 to 17. This method comprises the following successive steps.

Figure 6:
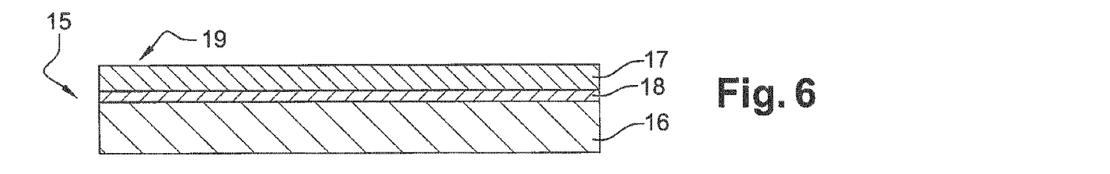

A first step, shown in FIG. 6, consists in providing a wafer 15 having a sandwich structure, which comprises a bottom layer 16, a top layer 17 and an insulating layer 18 located between said bottom and top layers 16, 17.

For example, said wafer 15 is a SOI (Silicon On Insulator) wafer having a diameter of 100 mm, a 380 μm thick bottom layer 16, a 1 μm thick insulating layer 18 and a 10 μm thick top layer 17. The top layer 17 and the bottom layer 16 are made of monocrystalline silicon, and the insulating layer 18 is made of silicon dioxide.

The method according to the invention further comprises a step of structuring the top layer 17 to define a three-dimensional structure on the top surface 19 of the top layer 17.

To this aim, a second step consists in applying a photosensitive resist layer 20 (FIG. 7) onto the top layer 17. In order to delineate the surface layout of the three-dimensional structure, the photosensitive resist layer 20 is illuminated with UV light through a mask (not shown), such as a chrome/glass mask. Open patterns in the mask corresponding to the three-dimensional structure layout provide a space-selective UV illumination. Photo initiators react and start polymerizing the resist layer where the resist has been space-selectively illuminated. Specific chemistry is then used to remove unexposed and unreacted resist. The remaining pattern of hardened resist 20 defines the shape of spacing elements 7a.

The photosensitive resist 20 may be positive or negative photoresist. One example for a positive resist is MICROPOSIT S 1805 PHOTO RESIST supplied by Shipley Company and one example for a negative photoresist is GM1040 SU-8 PHOTO EPOXY as supplied by Gersteltec Engineering Solutions. The photosensitive resist layer may be applied onto the wafer by different techniques known in the art, such as spray coating, or preferably spin coating.

Figure 7:
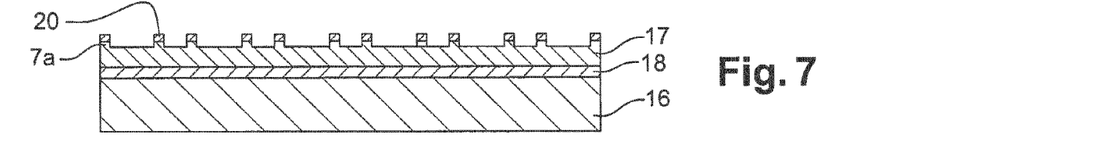

Then, as shown in FIG. 7, a third step consists in etching the top layer 17 on a part of its height only, to delineate spacing elements 7a protruding upward. This may be done by deep reactive silicon etching (DRIE), such as the Bosch process for deep silicon etching based on DRIE (Deep Reactive Ion Etching).

The Bosch process is disclosed in the document "J. K. Bhardwaj, H. Ashraf, Proc. SPIE, 2639, 224 (1995); A.

Schilp, M. Hausner, M. Puech, N. Launay, H. Karagoezoglu, F. Laermer, Advanced etch tool for high etch rate deep reactive ion etching in silicon micromachining production environment, Proceeding MST 2001, Dusseldorf". The Deep Reactive Ion Etching is disclosed in the document "Madou M J, 2002, Fundamentals of microfabrication, CRC Press".

Figure 8:
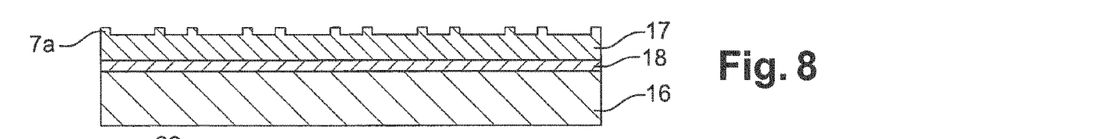

In a fourth step, shown in FIG. 8, the photosensitive resist 20 is removed in a wet chemical bath. Thus, it remains a clean monocristalline silicon layer 17 defining a series of spacing elements 7a.

A fifth step consists in applying another photosensitive resist layer 21 (FIG. 9) onto the top layer 17. In order to delineate the surface layout of the microcarriers, the photosensitive resist layer is illuminated with UV light through a mask (not shown), such as a chrome/glass mask. As previously, open patterns in the mask corresponding to the microcarriers layout provide a space-selective UV illumination. Photo initiators react and start polymerizing the resist layer where the resist has been space-selectively illuminated. Specific chemistry is then used to remove unexposed and unreacted resist. The remaining pattern of hardened resist 21 defines the outer shape of bodies 6 of the microcarriers 1.

In a preferred embodiment herein, the remaining pattern of hardened resist 21 further defines a code such as a binary code consisting of a series of through holes in the bodies 6 of the microcarriers 1, similar to the holes 2 and 3 shown in FIG. 1.

Figure 9:
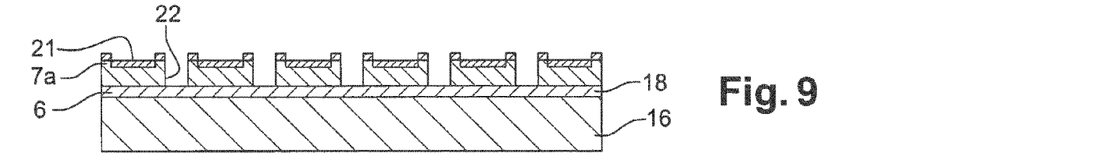

A sixth step, shown in FIG. 9, consists in etching away the top layer 17 to delineate the lateral walls 22 of the microcarriers 1. This may be done by deep reactive silicon etching (DRIE), such as the Bosch process for deep silicon etching based on DRIE (Deep Reactive Ion Etching).

Figure 10:
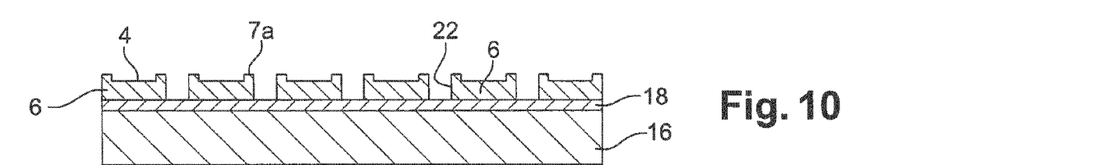

In a seventh step shown in FIG. 10, the photosensitive resist 21 is removed in a wet chemical bath. Thus, it remains a clean monocristalline silicon layer defining a series of bodies 6 that are patterned according to the design of the microcarriers 1.

Figure 11:
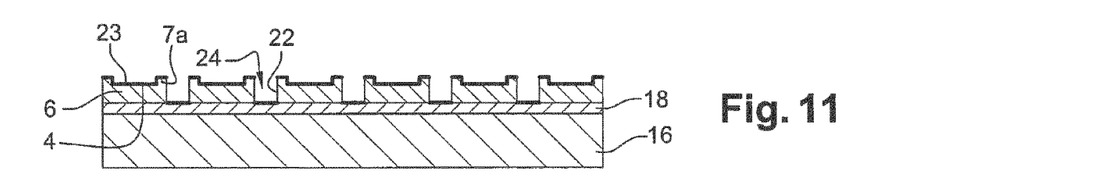

An eighth step, shown in FIG. 11, consists in depositing a first active layer 23 on the top surfaces 4 of the bodies 6. During the deposition, the first active layer 23 is also deposited in the bottom of the recesses 24 formed between the lateral walls 22.

The first active layer 23 is a layer having optical properties, such as an oxide layer comprising silicon dioxide. The thickness of the first layer 23 is approximately between 90 and 120 nm when working with red fluorescence labels. Any other dielectric material, such as a nitride, or a metal layer could also be used.

Different types of oxide deposition methods can be used such as PECVD (Plasma-enhanced chemical vapor deposition), evaporation, or sputtering (Madou M J, 2002, Fundamentals of microfabrication, CRC Press). For the deposition of silicon dioxide from PECVD technique, a mixture of gases such as dichlorosilane or silane and oxygen may be used, typically at pressures from a few hundred milliTorr to a few Torr. The deposition of the silicon dioxide is performed with a temperature comprised in a range from the room temperature to 300° C.

Figure 12:
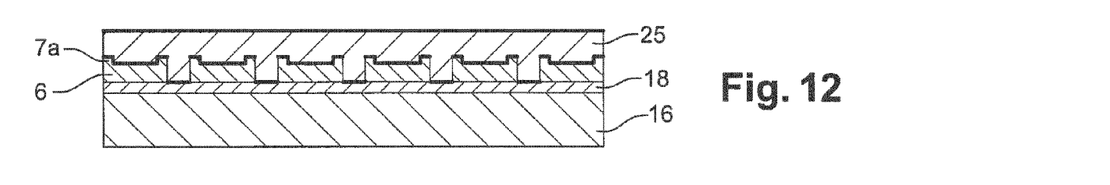

A ninth step, shown in FIG. 12, consists in applying a polymer 25 layer over the first active layer 23, for example a parylene layer or a layer made of a material known under the references ProTEK, AZ PC 520D or SX AR-PC 5000/40, respectively provided by the companies Brewer Science, Microchemical and Allresist. The thickness of said polymer layer 25 is preferably between 1 µm to 100 µm. This polymer layer is for example applied by Chemical Vapor Deposition (CVD) or by spin coating. A tenth step, shown in FIG. 13, consists in removing the bottom layer 16 and the insulating layer 18.

The etching away of the bottom layer 16 is performed by grinding a major portion of the bottom layer 16 and etching the rest of the bottom layer 16 by bath etching consisting in dipping the SOI wafer into a potassium hydroxide bath. Then, the insulating layer 18 is completely etched away by plasma etching of $CHF_3$ (fluoroform) or by plasma etching of $CF_4$. The etch rate of the insulating layer 18 is controlled.

The method according to the invention further comprises a step of structuring the bottom surface 5 of each body 6 to define three-dimensional structures on this bottom surface 5.

To this aim, an eleventh step consists in applying a photosensitive resist layer 26 (FIG. 14) onto the bottom surfaces 5 of the bodies 6. As previously, in order to delineate the surface layout of the three-dimensional structures, the photosensitive resist layer is illuminated with UV light through a mask (not shown), such as a chrome/glass mask. Open patterns in the mask corresponding to the three-dimensional structures layout provide a space-selective UV illumination. Photo initiators react and start polymerizing the resist layer where the resist has been space-selectively illuminated. Specific chemistry is then used to remove unexposed and unreacted resist. The remaining pattern of hardened resist 26 defines the shape of spacing elements 7b.

Then, as shown in FIG. 14, a twelfth step consists in etching the bottom surfaces 5 of the bodies 6 on a part of their height only, to delineate spacing elements 7b protruding downward. This may be done by deep reactive silicon etching (DRIE), such as the Bosch process for deep silicon etching based on DRIE (Deep Reactive Ion Etching).

In a thirteenth step, shown in FIG. 15, the photosensitive resist 26 is removed in a wet chemical bath.

In order to produce bi-layered microcarriers 1, the method according to the invention comprises an fourteenth step, shown in FIG. 16, which consists in depositing a second active layer 27 onto the bottom surfaces 5 of the bodies 6 of the microcarriers. The second active layer 27 has also optical properties, such as an oxide layer comprising silicon dioxide. The thickness of the second active layer 27 is approximately between 90 and 120 nm when working with red fluorescence labels. Any other dielectric material, such as a nitride, or a metal layer could also be used.

The second active layer 27 may be deposited with the same method used for the deposition of the first active layer 23.

Figure 17:
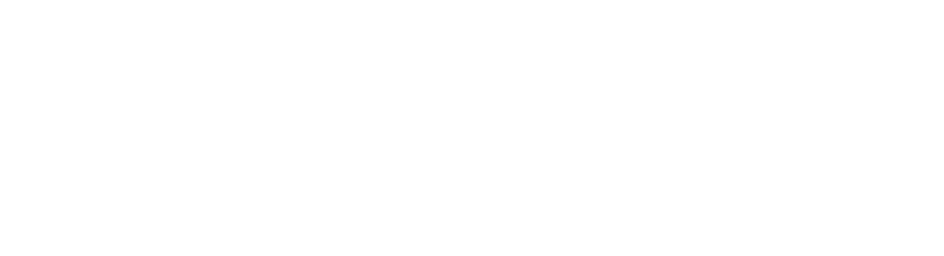

The polymer layer 25 is then etched away in order to separate and release the bi-layered microcarriers 1, as shown in FIG. 17, for example by oxygen plasma. The etch rate is controlled.

The released microcarriers 1 may be kept in suspension in liquid containers or vessels until use in an assay.

FIGS. 18 to 24 illustrate another embodiment of the method according to the invention.

In this embodiment, the wafer 15 shown in FIG. 11 is obtained with the same steps.

Figure 18:
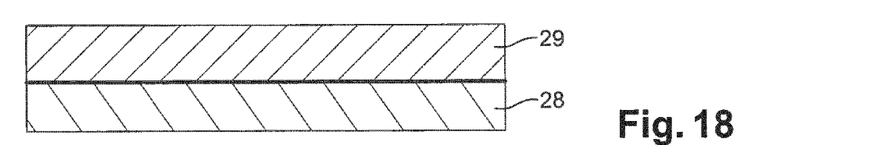
FIGS. 18 to 24 illustrate another embodiment of the invention.

Then, as shown in FIG. 18, a support 28 is covered with a layer of glue 29. The support 28 is for example a wafer made of silicon, quartz or glass and has a thickness about 300 to 700 µm. The glue 29 is for example a resin referenced Wafer-BOND HT10.10 or CR200 and provided by the company Brewer Science. The thickness of the glue layer 29 is about 10 to 100 µm, and is preferably about 50 µm.

Figure 19:
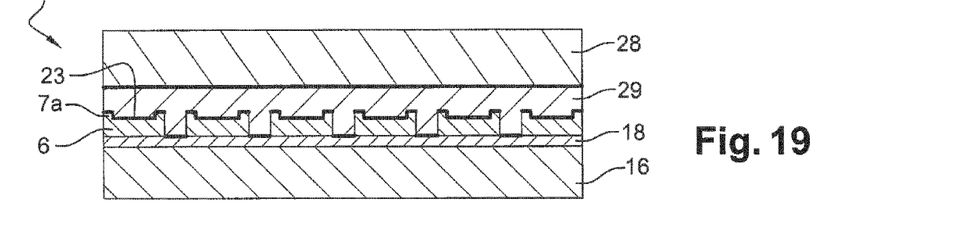

As shown in FIG. 19, the support 28 is then bound to the wafer 15 through the glue layer 29 which contacts and adheres to the first active layer 23. Such binding is preferably made by pressing and heating the wafer 15, the support 28 and the glue layer 29.

In a variant, the glue layer 29 is directly applied on the first active layer 23 and the support 28 is applied onto the glue layer 29.

Figure 20:
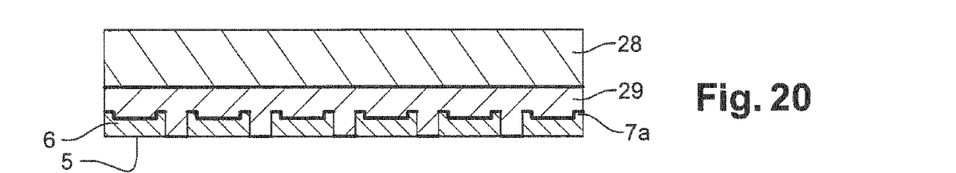
Figure 21:
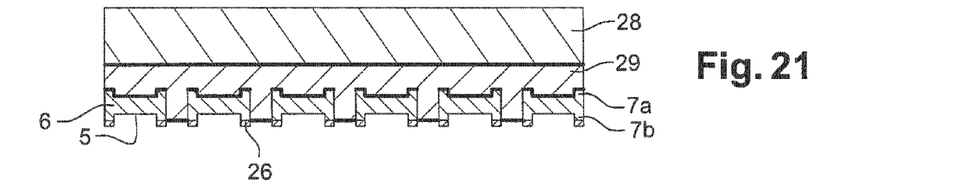
Figure 22:
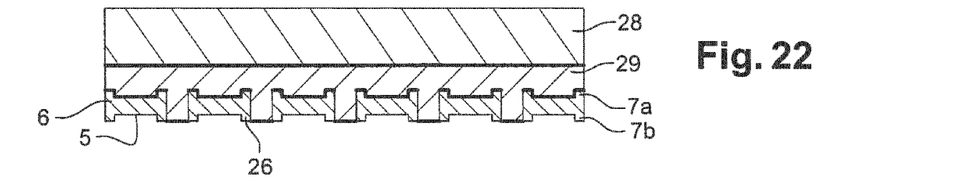

Another step, shown in FIG. 20, consists removing the bottom layer 16 by etching away the bottom layer and the insulating layer 18. This etching step is similar to the one performed in FIG. 13.

Then follows a step of structuring the bottom surface 5 of each body 6 to define three-dimensional structures on this bottom surface 5 (FIGS. 21 and 22), in a manner similar to the method involved in FIGS. 14 and 15.

Figure 23:
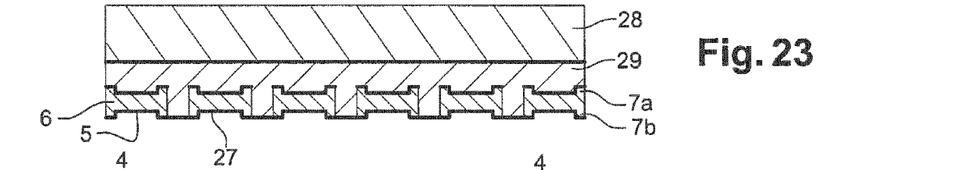

A second active layer 27 can then be deposited onto the bottom surface of the bodies 6 of the microcarriers (FIG. 23). Such deposition is made according to the method involved in FIG. 16.

Figure 24:
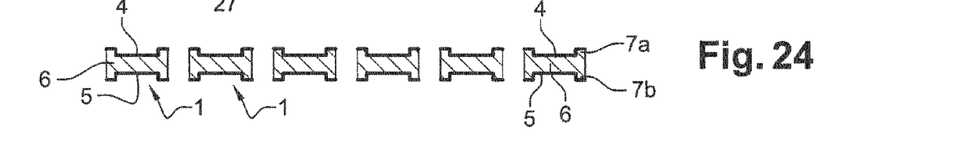

Then, the support 28 is separated from the wafer 15 by removing the glue layer 29. Such removal can be made by heating the glue layer 29 or by using a solvent. The bi-layered microcarriers 1 are thus separated and released, as shown in FIG. 24.

The support 28 provides enhanced mechanical properties in order to facilitate the handling of the wafer 15 during the production of the microcarriers.

Figure 25:
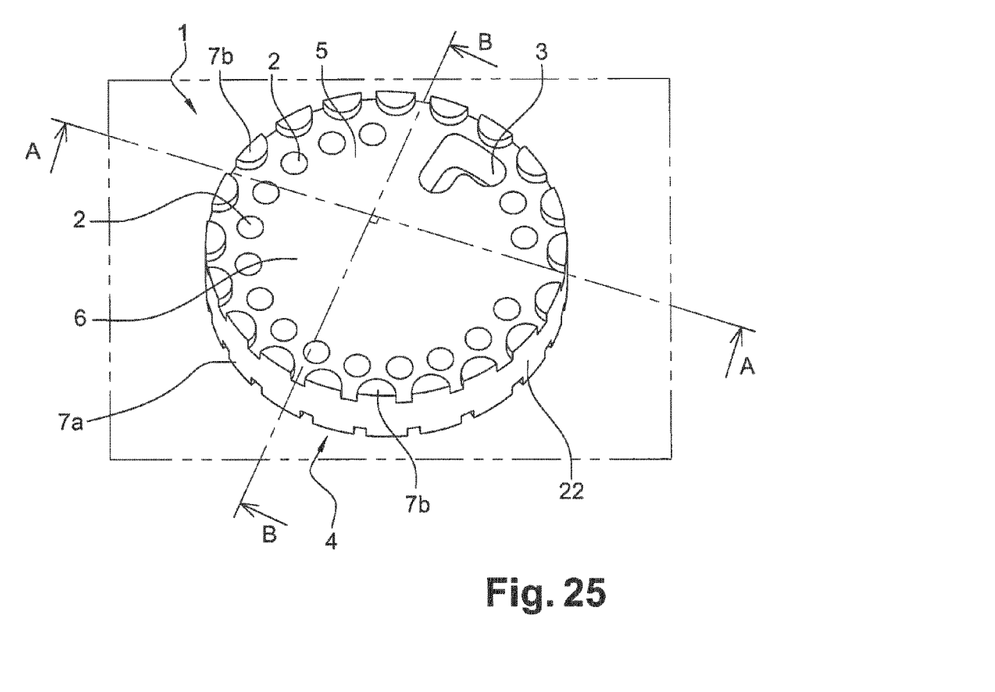
FIG. 25 illustrates a bottom perspective view of a microcarrier according to the invention.
Figure 26:
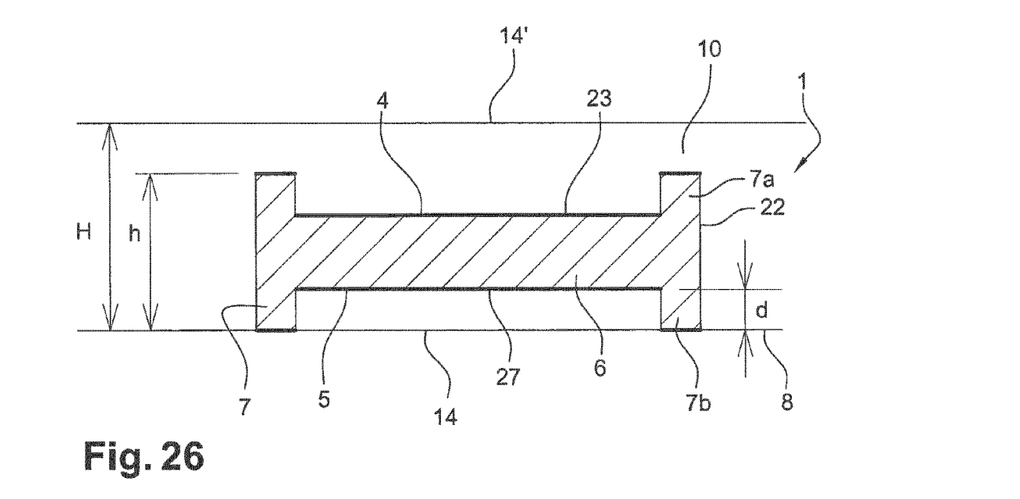
FIG. 26 illustrates a cross-section view of the microcarrier according to the invention in a microchannel.

FIGS. 25 and 26 illustrate a microcarrier 1 obtained by the above mentioned method and comprising a body 6 having a top surface 4 and a bottom surface 5. A first set of spacing elements 7a protrudes from the top surface 4 of the body 6. A second set of spacing elements 7b protrudes from the bottom surface 5 of the body 6. Each set comprises for example twenty spacing elements 7a, 7b.

Each spacing element 7a, 7b has a shape of a truncated right cylinder, is disposed on the periphery of the corresponding surface 4, 5 and extends in the continuation of the cylindrical lateral wall 22 of the body 6. Each circular right cylinder is truncated along its height by the cylindrical wall 22 of the microcarrier 1.

Alternatively, each spacing element 7a, 7b has a shape of a truncated cone or of a spike (not shown).

The surface of the spacing elements 7a, 7b represents less than 20% of the corresponding surface 4, 5, preferably less than 15%.

The microcarrier 1 with its spacing elements 7a, 7b is shaped to ensure that, when the microcarrier 1 is laid on a flat plane 14, a gap d exists between said flat plane 14 and the bottom or top surface 5, 4 of the body 6, as shown in FIG. 26.

Advantageously, the height of the gap d is less than 30% of the greatest height h of the encoded microcarrier 1 (FIG. 5). Most preferably, the distance d is greater than 5% of the height h, more preferably 10%. In the example of the figures, the Height h of the encoded microcarrier 1 is about 10 μm and the distance d is about 1 μm.

The microcarrier 1 also comprise a code comprising a distinctive pattern made of a plurality of traversing holes 2 and an asymmetric orientation mark such as, for example, a L-shaped sign 3 (as shown in FIG. 25) or a triangle. This asymmetric orientation mark allows the distinction between the top surface 4 and the bottom surface 5 of the body 6 of the microcarrier 1.

Each surface 4, 5 of the body 6 is also covered with a homogeneous and continuous active layer 23, 27.

Each microcarrier 1 is preferably shaped in the form of a disk having a diameter between 1 and 200 μm, for example 40 μm.

Each surface 4, 5 further has an area wherein, when the encoded microcarrier 1 is laid on the flat plane 14, each point of said area belongs to the two different cross-sections along the axis AA and BB, shown in FIG. 25, which are perpendicular to each other and to said plane 14. Said cross-sections AA and BB are free of spacing element 7a, 7b. This ensures that, when the microcarrier 1 lays flat against said flat plane 14 and is in a laminar flow essentially parallel to that flat plane 14, the orientation of the microcarrier 1 around an axis normal to the flat plane does not significantly affect the flow in the gap d. In other words, there is no preferred rotational orientation of the microcarrier 1 with regard to the flow, which would change the efficacy of a reaction.

The microcarrier 1 is also functionalized, or is adapted to be functionalized. Thus, one or more ligands or functional units are bound to the surfaces 4, 5 of the microcarrier 1 or impregnated in its bulk.

When such microcarrier 1 is used in an assay device similar to the one shown on FIG. 4, whatever the orientation of the microcarrier 1 in the microchannel 10, a gap always exists between the bottom surface 5, respectively the top surface 4 of the body 6 of the microcarrier 1, and the bottom surface 14, respectively the top surface 14' of the microchannel 10.

In addition, whatever the orientation of the microcarrier 1 in the microchannel 10, a functionalized surface provided with an active layer is always facing the bottom surface 14 of the microchannel 10, i.e. the observation wall through which the assay is monitored. When the assay is monitored by fluorescent signal, the observation wall 14 is transparent.

The gaps permit a homogeneous convective flow all over the microfluidic channel 10 and all over the functionalized surfaces 4, 5 of the body 6, resulting in a homogeneous fluorescent increase over time. Therefore, the analyte being flushed can be rapidly and reliably be quantified.

Other embodiments of the invention will be apparent to those skilled in the art from consideration of the specification and practice of the invention disclosed herein. It is intended that the specification and example be considered as exemplary only, with the true scope and spirit of the invention being indicated by the following claims.

Having described the invention, the following is claimed:

1. A method for producing microcarriers, the method comprising the following steps:
    (a) providing a wafer having a sandwich structure comprising a bottom layer, a top layer and an insulating layer located between said bottom and top layers,
    (b) structuring the top layer to define at least one three-dimensional structure on a top surface of the top layer,
    (c) etching away the top layer to delineate lateral walls of bodies of the microcarriers, each body comprising at least one three-dimensional structure on its top surface,
    (d) applying a continuous polymer layer over the top surface of the bodies of the microcarriers,
    (e) removing the bottom layer and the insulating layer,
    (f) structuring the bottom surfaces of the bodies of the microcarriers to define at least one three-dimensional structure on the bottom surface of each body, and
    (g) removing the polymer layer to release the microcarriers.

2. A method according to claim 1, further comprising a step of depositing a first layer on the top surfaces of the bodies of the microcarriers before step (d).

3. A method according to claim 2, wherein the first layer comprises a material having optical or magnetic properties, polycrystalline silicon and/or polytetrafluoroethylene, or a metallic layer having a high reflective index.

4. A method according to claim 3, wherein the first layer comprises an oxide or a nitride, or a metal layer.

5. A method according to claim 1, further comprising a step of depositing a second layer on the bottom surfaces of the bodies of the microcarriers before step (g).

6. A method according to claim 5, wherein the second layer comprises a material having optical or magnetic properties, polycrystalline silicon and/or polytetrafluoroethylene, or a metallic layer having a high reflective index.

7. A method according to claim 6, wherein the second layer comprises an oxide or a nitride, or a metal layer.

8. A method according to claim 7, wherein the oxide is silicon dioxide.

9. A method according to claim 1, wherein the three-dimensional structure of the top surface of each body and/or the three-dimensional structure of the bottom surface of each body comprises at least one spacing element protruding from the corresponding top and bottom surfaces.

10. A method according to claim 4, wherein the oxide is silicon dioxide.

11. A method according to claim 1, wherein the three-dimensional structure of the top surface of each body and/or the three-dimensional structure of the bottom surface of each body comprises at least one diffraction grating.

12. A method according to claim 1, wherein the three-dimensional structure of the top surface of each body and/or the three-dimensional structure of the bottom surface of each body comprises at least one nanostructure having a nanoscale depth.

13. A method according to claim 1, wherein the polymer layer comprises parylene.

14. A method according to claim 1, wherein the polymer layer is a glue layer which binds a support to the wafer.

15. A method according to claim 14, wherein said support is a wafer made of silicon, quartz or glass.

16. A method according to claim 1, wherein step (e) includes a first etching for etching selectively the bottom layer and a second etching for etching selectively the insulating layer.

17. A method according to claim 16, wherein said bottom layer is selectively etched by using an etching bath.

18. A method according to claim 16, wherein said insulating layer is selectively etched by a dry etching.

* * * * *